(12) United States Patent
McGrath

(10) Patent No.: US 7,272,431 B2
(45) Date of Patent: Sep. 18, 2007

(54) REMOTE-SENSING METHOD AND DEVICE

(75) Inventor: William R. McGrath, Monrovia, CA (US)

(73) Assignee: California Institute of Technology, Pasadena, CA (US)

( * ) Notice: Subject to any disclaimer, the term of this patent is extended or adjusted under 35 U.S.C. 154(b) by 485 days.

(21) Appl. No.: 10/632,347

(22) Filed: Aug. 1, 2003

(65) Prior Publication Data

US 2004/0123667 A1 Jul. 1, 2004

Related U.S. Application Data

(60) Provisional application No. 60/473,670, filed on May 23, 2003, provisional application No. 60/400,399, filed on Aug. 1, 2002.

(51) Int. Cl.
*A61B 5/04* (2006.01)
(52) U.S. Cl. ..................................... 600/509
(58) Field of Classification Search ............... 600/407, 600/509
See application file for complete search history.

(56) References Cited

U.S. PATENT DOCUMENTS

| 4,958,638 | A | * | 9/1990 | Sharpe et al. ............. 600/407 |
| 5,030,956 | A | | 7/1991 | Murphy |
| 5,105,354 | A | | 4/1992 | Nishimura |
| 5,226,425 | A | | 7/1993 | Righter |
| 5,227,797 | A | | 7/1993 | Murphy |
| 5,448,501 | A | * | 9/1995 | Hablov et al. ............ 340/573.1 |
| 5,507,291 | A | | 4/1996 | Stirbl et al. |
| 5,606,971 | A | | 3/1997 | Sarvazyan |
| 5,760,687 | A | * | 6/1998 | Cousy ....................... 340/554 |
| 5,931,791 | A | | 8/1999 | Saltzstein et al. |
| 6,011,477 | A | | 1/2000 | Teodorescu et al. |
| 6,031,482 | A | * | 2/2000 | Lemaitre et al. ............ 342/22 |
| 6,062,216 | A | | 5/2000 | Corn |
| 6,083,172 | A | | 7/2000 | Baker, Jr. et al. |
| 6,122,537 | A | * | 9/2000 | Schmidt ..................... 600/407 |
| 6,129,675 | A | | 10/2000 | Jay |
| 6,132,371 | A | | 10/2000 | Dempsey et al. |

(Continued)

FOREIGN PATENT DOCUMENTS

EP  1 188 412 A2  3/2002

(Continued)

OTHER PUBLICATIONS

Clark et al., "Medical Instrumentation Application And Design", John Wiley & Sons, Inc., undated, Third Edition, Section 4.6 through 6.6, pp. 139-259, Cover page (1).

(Continued)

*Primary Examiner*—George Manuel
*Assistant Examiner*—Christopher A. Flory
(74) *Attorney, Agent, or Firm*—Christie, Parker & Hale, LLP

(57) ABSTRACT

Apparatus and methods for performing remote detection of physiological activity are described. One aspect of the invention involves obtaining information concerning respiration and heart function. In one embodiment, the invention includes a source containing an oscillator configured to illuminate the subject with electromagnetic signal beam and a receiver configured to observe changes in the amplitude of the electromagnetic signal reflected by the subject.

12 Claims, 9 Drawing Sheets

U.S. PATENT DOCUMENTS

| | | | |
|---|---|---|---|
| 6,208,286 B1 * | 3/2001 | Rostislavovich et al. | ... 342/135 |
| 6,254,551 B1 | 7/2001 | Varis | |
| 6,289,238 B1 | 9/2001 | Besson et al. | |
| 6,315,719 B1 | 11/2001 | Rode et al. | |
| 6,325,761 B1 | 12/2001 | Jay | |
| 6,332,087 B1 * | 12/2001 | Svenson et al. | ............ 600/407 |
| 6,359,597 B2 * | 3/2002 | Haj-Yousef | ................. 343/850 |
| 6,434,411 B1 | 8/2002 | Duret | |
| 6,454,708 B1 | 9/2002 | Ferguson et al. | |
| 6,478,744 B2 | 11/2002 | Mohler | |
| 6,753,780 B2 * | 6/2004 | Li | ........................... 340/573.1 |
| 2002/0028991 A1 | 3/2002 | Thompson | |
| 2004/0019261 A1 | 1/2004 | Gopinathan et al. | |

FOREIGN PATENT DOCUMENTS

| | | |
|---|---|---|
| WO | WO93/19667 | 10/1993 |
| WO | WO 02/05700 A2 | 1/2002 |

OTHER PUBLICATIONS

Geddes et al., "Principles Of Applied Biomedical Instrumentation", Wiley-Interscience Publication, Third Edition, undated, pp. 600-613, cover page (1).

IEEE Standards Coordinating Committee 28, "IEEE Standard For Safety Levels With Respect To Human Exposure To Radio Frequency Electromagnetic Fields, 3kHz to 300 GHz", IEEE Std. C95.1, Apr. 16, 1999, pp. 1-73, Cover pg. (1), Abstract (2 pgs), Introduction (6 pgs), Table of Contents (1 pg).

Behnia et al., "Closed-Loop Feedback Control Of Phased-Array Microwave Heating Using Thermal Measurements From Magnetic Resonance Imaging", Concepts in Magnetic Resonance (Magnetic Resonance Engineering), vol. 15, No. 1, 2002, pp. 101-110.

Osepchuk, J., "How Safe Are Microwaves And Solar Power From Space?", IEEE Microwave Magazine, Dec. 2002, pp. 58-64.

Yan et al., "Theoretical Analysis Of The Biological Thermal Effect Of Millimeter Waves In Layered-Dielectric-Slabs", International Journal Of Infrared and Millimeter Waves, vol. 24, No. 5, May 2003, pp. 763-772.

Vijayalaxmi et al., "Genotoxic Potential Of 1.6 GHz Wireless Communication Signal: In Vivo Two-Year Bioassay", Radiation Research, vol. 159, 2003, pp. 558-564.

Bit-Babik et al., "Estimation Of The SAR In The Human Head And Body Due To Radiofrequency Radiation Exposure From Handheld Mobile Phones With Hands-Free Accessories", Radiation Research, vol. 159, 2003, pp. 550-557.

Thalau et al., "Temperature Changes In Chicken Embryos Exposed To A Continuous-Wave 1.25 GHz Radiofrequency Electromagnetic Field", Radiation Research, vol. 159, 2003, pp. 685-692.

Hirata et al., "Correlation Of Maximum Temperature Increase and Peak SAR In The Human Head Due to Handset Antennas", IEEE Transactions On Microwave Theory and Techniques, vol. 51, No. 7, Jul. 2003, pp. 1834-1841.

Lin et al., "Wearable Sensor Patches For Physiological Monitoring", JPL Inventor's Report, NASA Case No. 0246 20651, NASA Tech Brief vol. 25, No. 2, pp. 1-3, cover pgs (2).

Patterson, R. "Fundamentals Of Impedance Cardiography", IEEE Engineering In Medicine and Biology Magazine, Mar. 1989, pp. 35-38.

Wang et al., "Multiple Sources Of The Impedance Cardiogram Based On 3-D Finite Difference Human Thorax Models", IEEE Transactions on Biomedical Engineering, vol. 42, No. 2, Feb. 1995, pp. 141-148.

Patterson et al., "Impedance Cardiography Using Band And Regional Electrodes In Supine, Sitting, And During Exercise", IEEE Transactions on Biomedical Engineering, vol. 38, No. 5, May 1991, pp. 393-400.

Jossinet, J., "The Impedivity Of Freshly Excised Human Breast Tissue", Physiol. Meas., vol. 19, 1998, pp. 61-75.

Mohapatra et al., "Blood Resistivity And Its Implications For The Calculation Of Cardiac Output By The Thoracic Electrical Impedance Technique", Intens. Care Med., vol. 3, 1977, pp. 63-67.

King R., "Comments On "Biological Effects Of Radio-Frequency/Microwave Radiation"", IEEE Transactions on Microwave Theory and Techniques, vol. 50, No. 8, Aug. 2002, pp. 2032-2033.

King, R., "Electric Fields Induced In Cells In The Bodies Of Amateur Radio Operators By Their Transmitting Antennas", IEEE Transactions On Microwave Theory and Techniques, vol. 48, No. 11, Nov. 2000, pp. 2155-2158.

King, R., "Electric Current And Electric Field Induced In The Human Body When Exposed To An Incident Electric Field Near The Resonant Frequency", IEEE Transactions on Microwave Theory And Techniques, vol. 48, No. 9, Sep. 2000, pp. 1537-1543.

Johnson et al., "Nonionizing Electromagnetic Wave Effects In Biological Materials And Systems", Proceedings of the IEEE, vol. 60, No. 6, Jun. 1972, pp. 692-719.

Lohman et al., "A Digital Signal Processor For Doppler Radar Sensing Of Vital Signs", 2001 Proceedings of the 23rd Annual EMBS International Conference, Oct. 25-28, 2001, Istanbul, Turkey, pp. 3359-3362.

Guillen et al., "Design Of A Prototype For Dynamic Electrocardiography Monitoring Using GSM Technology: GSM-Holter", 2001 Proceedings of the 23rd Annual EMBS International Conference, Oct. 25-28, 2001, Istanbul, Turkey, pp. 3956-3959.

Marbán, E., "Cardiac Channelopathies", Insight Review Articles, undated, 6 pgs.

Boric-Lubecke et al, "Wireless House Calls: Using Communications Technology For Health Care And Monitoring", IEEE Microwave Magazine, Sep. 2002, pp. 43-48.

Holden, A., "A Last Wave From The Dying Heart", Nature, vol. 392, Mar. 5, 1998, pp. 20-21.

Abubakar et al., "Imaging Of Biomedical Data Using A Multiplicative Regularized Contrast Source Inversion Method", IEEE Transactions on Microwave Theory and Techniques, vol. 50, No. 7, Jul. 2002, pp. 1761-1771.

Yu et al., "Can Millimeter Waves Generate Electroporation?", International Journal of Infrared and Millimeter Waves, vol. 23, No. 8, Aug. 2002, pp. 1261-1269.

Yu et al., "Discussion About The Ratio Method For Measuring Millimeter Wave Absorption By Biological Entities", International Journal of Infrared and Millimeter Waves, vol. 23, No. 7, Jul. 2002, pp. 997-1006.

McGill et al., "A Model Of The Muscle Action Potential For Describing The Leading Edge, Terminal Wave, And Slow Afterwave", IEEE Transactions on Biomedical Engineering, vol. 48, No. 12, Dec. 2001, pp. 1357-1365.

Adair et al., "Biological Effects Of Radio-Frequency/Microwave Radiation", IEEE Transactions on Microwave Theory and Techniques, vol. 50, No. 3, Mar. 2002, pp. 953-962.

Emili et al., "Computation Of Electromagnetic Field Inside A Tissue At Mobile Communications Frequencies", IEEE Transactions on Microwave Theory and Techniques, vol. 51, No. 1, Jan. 2003, pp. 178-186.

Lin, J., "Noninvasive Microwave Measurement Of Respiration", Proceedings Of the IEEE, Oct. 1975, p. 1530.

Lee et al., "Magnetic Gradiometer Based On A High-Transition Temperature Superconducting Quantum Interference Device For Improved Sensitivity Of A Biosensor", Applied Physics Letters, vol. 81, No. 16, Oct. 14, 2002, pp. 3094-3096.

Pedersen et al., "An Investigation Of The Use Of Microwave Radiation For Pulmonary Diagnostics", IEEE Transactions on Biomedical Engineering, Sep. 1976, pp. 410-412.

Chen et al., "An X-Band Microwave Life-Detection System", IEEE Transactions on Biomedical Engineering, vol. BME-33, No. 7, Jul. 1986, pp. 697-701.

Lin et al., "Microwave Apexcardiography", IEEE Transactions on Microwave Theory and Techniques, vol. MTT-27, No. 6, Jun. 1979, pp. 618-620.

Rhee, et al., "An Ultra-Low Power, Self-Organizing Wireless Network And Its Applications To Non-Invasive Biomedical Instrumentation", IEEE/Sarnoff Symposium on Advances in Wired and Wireless Communications, Mar. 13, 2002, pp. 64-67.

Prance, et al., "An Ultra-Low-Noise Electrical-Potential Probe For Human-Body Scanning", Meas. Sci. Technol., vol. 11, 2000, pp. 291-297.

Clippingdale et al., "Ultrahigh Impedance Capacitively Coupled Heart Imaging Array", Rev. Sci. Instrum, vol. 65, No. 1, Jan. 1994, pp. 269-270.

Stanley et al., "Pressure-Jump Relaxation Apparatus Using Bipolar-Pulse Conductivity Detection", Rev. Sci. Instrum., vol. 65, No. 1, Jan. 1994, pp. 199-203.

Harland et al., "Electric Potential Probes—New Directions In the Remote Sensing Of The Human Body", Meas. Sci. Technol., vol. 13, 2002, pp. 163-169.

Harland et al., "Remote Detection of Human Electroencephalograms using Ultrahigh Input Impedance Electric Potential Sensors", Applied Physics Letters, vol. 81, No. 17, Oct. 21, 2002, pp. 3284-3286.

Ludwig, H., "Technical Note: Heart- Or Respiration-Rate Calculator", Med. & Biol. Eng. & Comput., vol. 15, 1977, pp. 700-702.

Spinelli et al., "A Novel Fully Differential Biopotential Amplifier With DC Suppression", IEEE Transactions on Biomedical Engineering, vol. 51, No. 8, Aug. 2004, pp. 1444-1448.

Lebedeva, A., "The Use Of Millimeter Wavelength Electromagnetic Waves In Cardiology", Critical Reviews™ in Biomedical Engineering, vol. 28, Nos. 1 and 2, 2000, pp. 339-347.

Taylor et al., "Precision Digital Instrument for Calculation Of Heart Rate and *R-R* Interval", IEEE Transactions On Biomedical Engineering, May 1975, pp. 255-257.

Droitcour et al, "21.1 0.25μm CMOS and BiCMOS Single-Chip Direct-Conversion Doppler Radars For Remote Sensing Of Vital Signs", ISSCC 2002, Session 21, TD: Sensors and Microsystems, Feb. 6, 2002, 2 pgs.

Droitcour et al., "Range Correlation Effect On ISM Band I/Q CMOS Radar For Non-Contact Vital Signs Sensing", IEEE MTT-S Digest, 2003, pp. 1945-1948.

Droitcour et al., "A Microwave Radio For Doppler Radar Sensing Of Vital Signs", undated, 4 pgs.

Hobbie R., "The Electrocardiogram As An Example Of Electrostatics", AJP, vol. 41, Jun. 1973, pp. 824-831.

Hobbie, R., "Improved Explanation Of The Electrocardiogram", Reprinted from American Journal of Physics, vol. 52, 1984, pp. 704-705, Energetics, pp. 234-235.

Liebe, H., "Mini-Review: Atmospheric EHF Window Transparencies Near 35, 90, 140 And 220 GHz", IEEE Transactions On Antennas And Propagation, vol. AP-31, No. 1, Jan. 1983, pp. 127-135.

Byrd, R., "NPO-30697: Non-Contact Electrocardiograph Machine", Opportunity Assessment Prepared for NASA Jet Propulsion Laboratory, Dec. 6, 2002, 40 pgs.

McNamee et al, "Short Communication: No Evidence for Genotoxic Effects from 24 H Exposure Of Human Leukocytes To 1.9 Radiofrequency Fields", Radiation Research, vol. 159, 2003, pp. 693-697.

\* cited by examiner

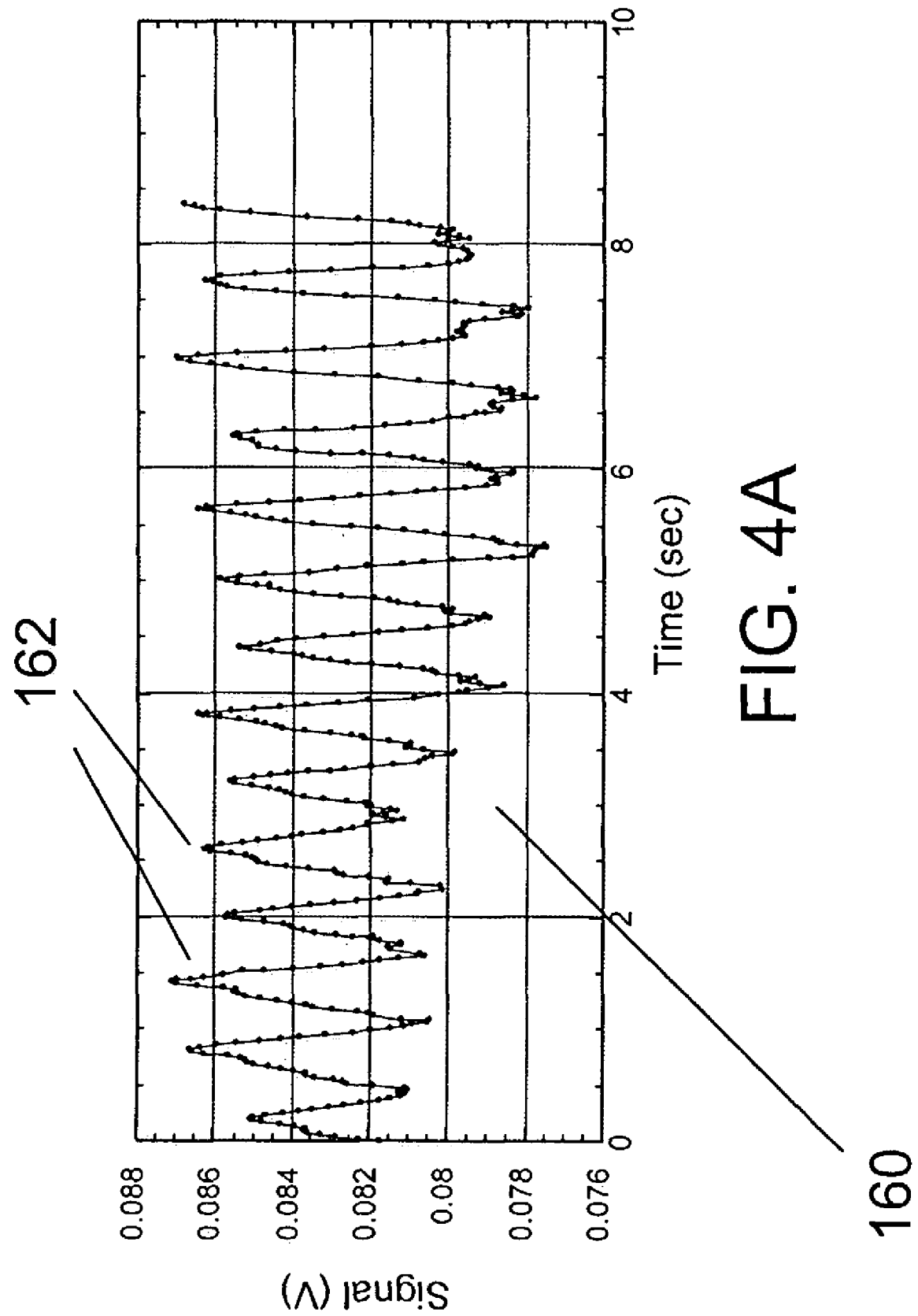

REMOTE-SENSING METHOD AND DEVICE

CROSS-REFERENCE TO RELATED APPLICATION

This application claims priority based on U.S. Provisional Application No. 60/400,399, filed Aug. 1, 2002, and U.S. Provisional Application No. 60/473,670 filed May 23, 2003, the disclosure of which is incorporated herein by reference.

STATEMENT REGARDING FEDERALLY SPONSORED RESEARCH OR DEVELOPMENT

The U.S. Government has certain rights in this invention pursuant to NAS7-1407 provided by the National Aeronautics and Space Administration, Office of Space Science.

BACKGROUND OF THE INVENTION

Information concerning a patient's breathing and heart function can be vital to the diagnosis and monitoring of many medical conditions. A electrocardiograph is a device that is commonly used to provide information concerning heart function. Electrocardiographs provide outputs that are indicative of electric fields created by the heart as it beats. Operation of an electrocardiograph typically requires attachment of nine leads, which are combined to obtain twelve sets of measurements. A large body of clinical experience has been amassed which has revealed correlations between specific shapes in the output of an electrocardiograph and many different types of heart conditions.

SUMMARY OF THE INVENTION

Embodiments of the present invention are capable of detecting physiological activity. In one aspect of the invention, motion can be detected. In another aspect, specific physiological activity such as respiration, heart rate or the electrophysiology of a heart can be monitored. In one embodiment adapted for monitoring the physiological activity of a subject, the invention includes a source containing an oscillator configured to illuminate the subject with an electromagnetic signal beam and a receiver configured to observe changes in the amplitude of the electromagnetic signal reflected by the subject.

In a further embodiment, the invention includes an RF oscillator connected to a first antenna portion, where the RF oscillator and the first antenna portion are configured to generate a electromagnetic signal beam that illuminates the subject and a detector connected to a second antenna portion, where the second antenna portion and detector are configured to generate a signal indicative of the amplitude of the electromagnetic signal reflected by the subject.

One embodiment of the method of the invention includes illuminating an area with an electromagnetic signal having a wavelength that renders at least some debris transparent and detecting the amplitude of reflections of the electromagnetic signal and observing variations in the amplitude.

A further embodiment of the invention includes illuminating the subject with an electromagnetic signal beam and observing changes in the amplitude of the electromagnetic signal reflected by the subject.

Another embodiment of the method of the invention for generating an electrocardiogram includes illuminating a heart with an electromagnetic signal beam and detecting the amplitude of the electromagnetic signal reflected by the heart.

BRIEF DESCRIPTION OF THE DRAWINGS

FIG. 4A is a graph illustrating the amplitude of the reflected electromagnetic signal measured in accordance with an embodiment of the present invention from a distance of two feet;

DETAILED DESCRIPTION OF THE INVENTION

Embodiments of the present invention use reflected electromagnetic signals to observe breathing, pulse and/or to generate an electrocardiogram of a subject. Other embodiments of the invention can be used to make observations concerning the function of neurons or other tissue types that are capable of generating an electric field. Remote-detection systems in accordance with the present invention typically work by using an RF oscillator to generate an electromagnetic signal beam that is then used to illuminate a subject. In operation, the subject's breathing, motion of the subject's heart beating and the depolarization and repolarization of the heart cells that accompany each heart beat can all contribute to variations in the amplitude of the electromagnetic signal reflected by the subject. An output indicative of the amplitude of the signal reflected by the subject is generated and signal processing techniques can be performed to extract the portions of the output that are indicative of the respiration rate, the pulse rate and/or the electrocardiogram of the subject.

Figure 1:
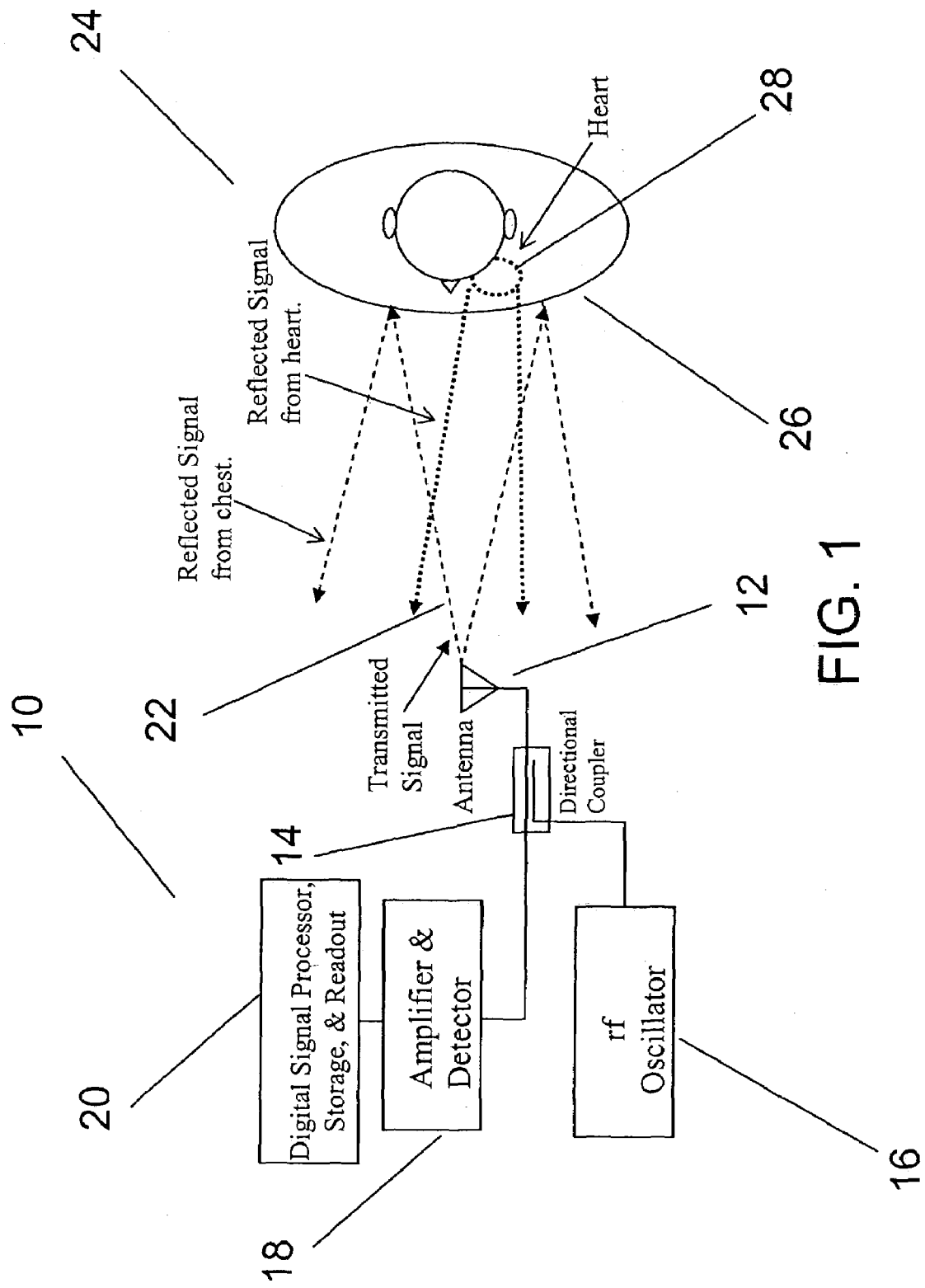
FIG. 1 is a schematic view of a remote-detection system in accordance with an embodiment of the present invention illuminating a subject with an electromagnetic signal.

Turning now to the diagrams, FIG. 1 illustrates a remote-detection system 10 in accordance with the present invention that includes an antenna 12 coupled via a directional coupler 14 to an RF oscillator 16 and a RF detector 18. In addition, the RF detector is connected to a digital signal processor 20. The RF Oscillator and the antenna can illuminate a subject 24 with an electromagnetic beam 22. The subject typically reflects a portion of the incident electromagnetic signal and the antenna and the RF detector can be used to generate a signal indicative of the amplitude of the reflected signal.

Information can then be extracted from the signal generated by the antenna and the RF detector by the digital signal processor 20.

When a subject is illuminated with an electromagnetic signal generated by a remote-detection system 10 in accordance with the present invention, the electromagnetic signal can be reflected as a result of the signal encountering a boundary between materials having different complex impedances. The complex impedance of a material is the property that determines the change in amplitude and phase shift of an electromagnetic wave reflected at an interface between that material and another material. The complex impedance of a material may change with the introduction or removal of free charge on the surface of the material. In the illustrated embodiment, the subject is a human and the electromagnetic signal beam 22 illuminates the subject's chest 26. Air has a comparatively low complex impedance compared to the complex impedance of human tissue. Therefore, a significant amount of any electromagnetic signal illuminating a human subject will be reflected by the subject's body. The pattern of the reflected signal will depend on the shape of the subject's body. Changes in the shape or position of a subject's chest associated with respiration can alter the pattern of the reflected signal in ways that can be observed using the antenna.

A beam 24 with appropriate intensity can illuminate a subject's heart 28. The amount of the electromagnetic signal reflected by the heart depends upon the complex impedance of the heart cells, which changes as the heart beats. When the heart beats, the heart cells are initially polarized due to an imbalance in the concentration of ions on either side of the cell membrane. As the heart muscles contract, the cell membranes of the heart muscle cells become permeable and the concentration of ions on either side of the membrane balances. All of the heart muscle cells do not depolarize simultaneously. Rather, a depolarization wave sweeps across the heart starting in the atria and moving to the ventricles. Once the heart has finished contracting, the heart muscle cells repolarize. The imbalance of ions on either side of a the cell membranes of polarized heart cells gives them a complex impedance that is significantly different to that of the tissue surrounding the heart. Therefore, electromagnetic signals will be reflected by polarized heart cells. The depolarization of heart muscle cells changes the complex impedance of the heart cells. Consequently, the motion of the heart and the depolarization and repolarization of the heart muscle cells will both have an effect on the pattern of electromagnetic signals reflected by the heart. Observing the changes in reflections from the heart over time in accordance with the present invention can provide information about the frequency with which the heart beats and the electrophysiology of the heart.

Figure 2:
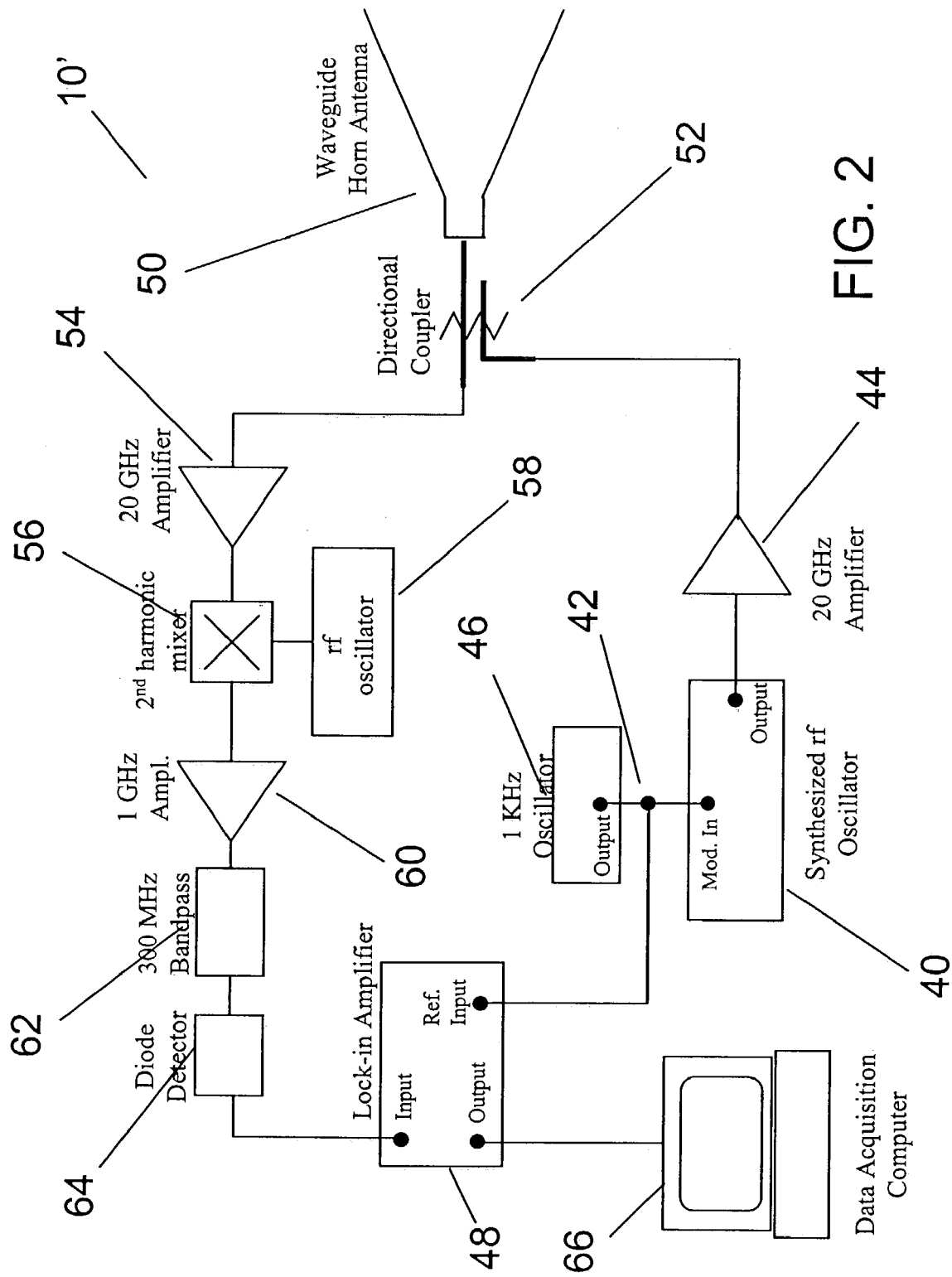
FIG. 2 is a block diagram of the components of a system in accordance with an embodiment of the present invention.

A block diagram of a remote-detection system in accordance with the present invention is illustrated in FIG. 2. The remote-detection system 10' includes a synthesized RF oscillator 40 that is connected to a common node 42 and a first amplifier 44. The common node 42 is connected to an oscillator 46 and a lock-in amplifier 48. The output of the first amplifier 44 is connected to an antenna 50 via a directional coupler 52. The directional coupler is also connected to a second amplifier 54. The output of the amplifier is connected to a mixer 56. An RF oscillator 58 also provides an output to the mixer. The output of the mixer is connected to the input of a third amplifier 60. The output of the third amplifier is connected to a bandpass filter 62 and the output of the bandpass filter is connected to a diode detector. An output of the diode detector is connected to an input of the lock-in amplifier 48 and the output of the lock-in amplifier is then provided to a data acquisition computer 66.

In one embodiment, the synthesized RF oscillator 40 produces an electromagnetic signal in the range of 20 GHz and can be implemented using a Model 33120A manufactured by Hewlett-Packard Company of Palo Alto, Calif. The first amplifier 44 boosts the strength of the signal and is implemented using a 2-20 GHz amplifier such as a Model 8349B manufactured by the Hewlett-Packard Company. The oscillator 46 generates a kilohertz range modulation signal and is implemented using a Model 83723B manufactured by Hewlett-Packard Company. The lock-in amplifier 48 synchonously detects the kilohertz amplitude-modulated output from the diode detector 64 and can be implemented using a Model SR830 manufactured by Stanford Research Systems of Sunnyvale, Calif. The waveguide horn antenna 50 produces the radiated signal beam and is implemented using a Model 639 manufactured by the Narda division of L-3 Communications Corporation of New York, N.Y. The directional coupler 52 couples the signal to be radiated to the antenna 50 and is implemented using a Model P752C-10 dB manufactured by the Hewlett-Packard Company. The second amplifier 54 provides a low-noise amplification of the reflected signal and is implemented using a 20 GHz amplifier such as a Model AMF-3D-000118000-33-10P manufactured by MITEQ, Inc. of Hauppauge, N.Y. The 2nd harmonic mixer 56 down-converts the signal to 1 GHz and can be implemented using a Model SBE0440LW1 manufactured by MITEQ, Inc. The RF oscillator 58 serves as the local oscillator for the mixer 56 and is implemented using a Model 8340A manufactured by Hewlett-Packard. The third amplifier 60 boosts the signal to a level aappropriate for the diode detector 64 and can be implemented using a 1 GHz amplifier such as a Model 4D-00011800-33-10P manufactured by MITEQ, Inc. The bandpass filter 62 limits the signal reception bandwidth in order to reduce the noise of the detection system and can be implemented using a 300 MHz bandpass filter such as a Model 381-1390-50S11 manufactured by Reactel, Incorporated of Gaithersburg, Md. The diode detector 64 produces a video response proportional to the amplitude of the reflected electromagnetic signal and can be implemented using a Model 8473C manufactured by the Hewlett-Packard Company. The data acquisition computer 66 digitizes the output of the lock-in amplifier 48, stores the signal, and displays it in a graphical format and can be implemented using a Macintosh Model 8600/300 manufactured by Apple Computer, Inc. of Cupertino, Calif.

As discussed above, the depolarization and repolarization of the heart generates an electric field and changes the complex impedance of the heart. The electric field generated by the heart can be modeled as a dipole moment. The dipole moment of the heart is created as a result of a portion of the heart being polarized and a portion of the heart being depolarized. Therefore, the changes in strength and direction of the dipole moment of the heart provide information concerning the electrophysiology of the heart. The dipole of the heart during the depolarization of the atria generates a P-wave on an electrocardiograph. The dipole of the heart during the depolarization of the ventricles generates a series of waves on the output of an electrocardiograph known as the "QRS complex". The change in dipole associated with the repolarization of the ventricles generates an output on an electrocardiograph known as a T-wave. These waves and complexes are commonly used in medical diagnosis. A further description of the electric field and physiology of the heart as it beats is described in the paper published by R. K. Hobbie in the American Journal of Physics, vol. 41, p.824

(1973) entitled "The Electrocardiogram as an Example of Electrostatics", which is incorporated herein by reference in its entirety.

Figure 3A:
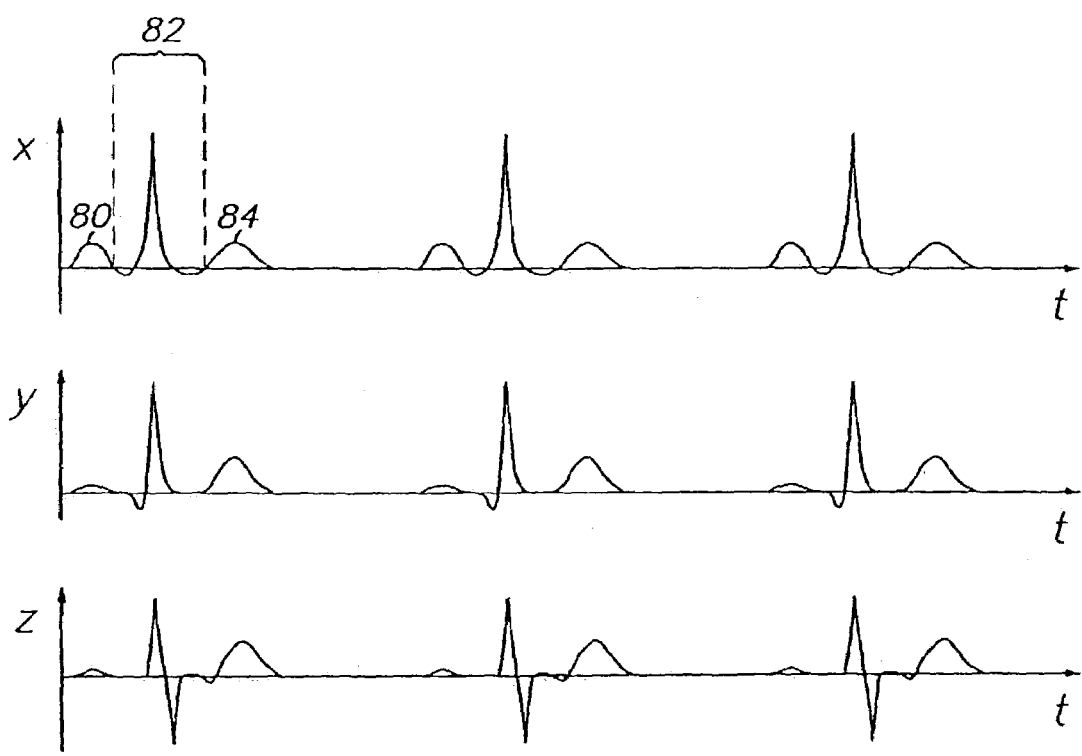
FIG. 3A is a schematic illustration of three orthogonal components of the dipole of a heart during depolarization and repolarization.

Orthogonal components of the dipole moment of the electric field generated by a heart during two successive beats are illustrated in FIG. 3A. The magnitude of the orthogonal components of the electric field during the P wave (80), the QRS complex (82) and the T wave (84) are indicated on the graph representing the x, y, and z-components of the electric field.

Figure 3B:
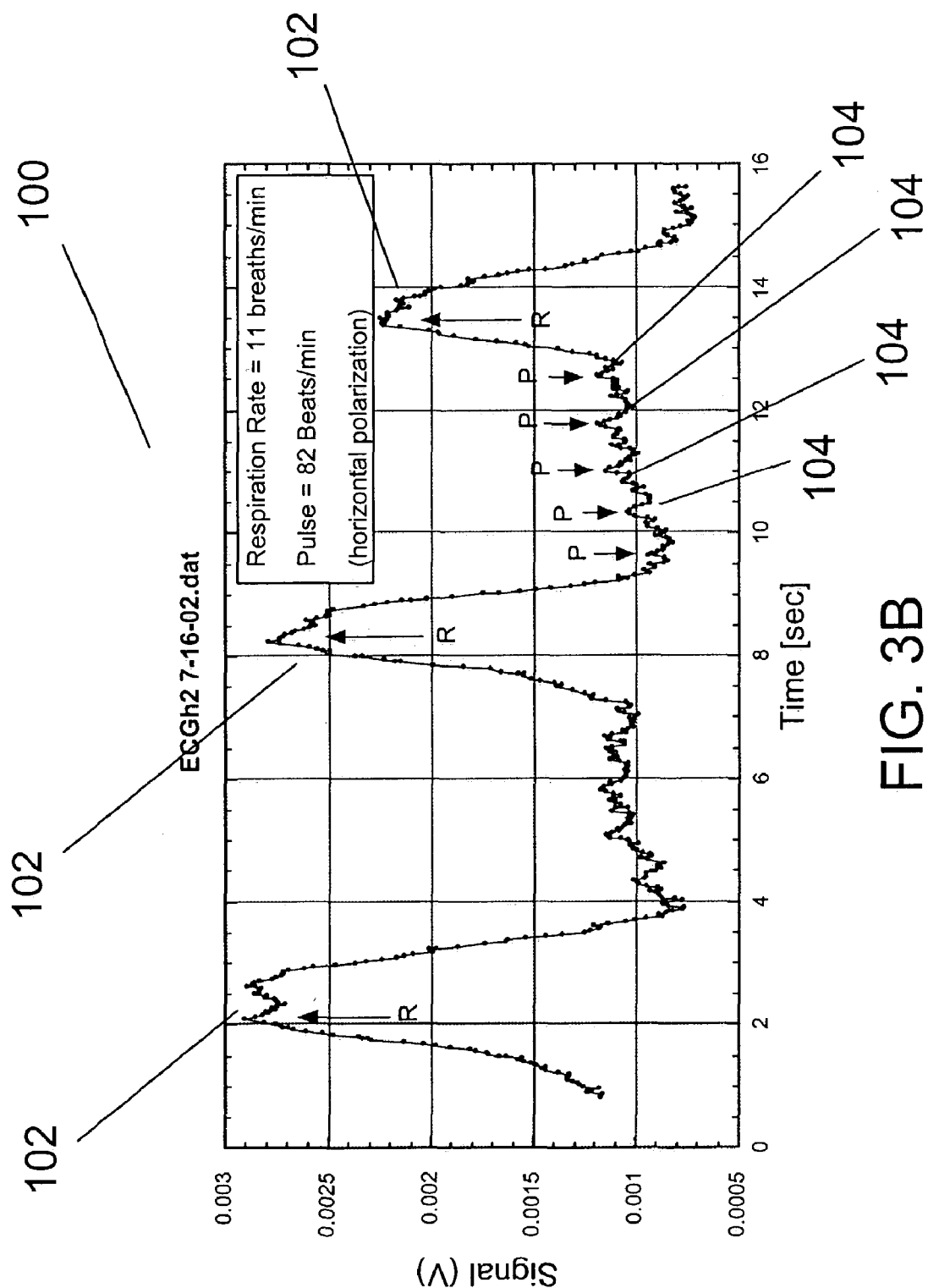
FIG. 3B is a graph showing the amplitude of reflected electromagnetic signal measured in accordance with an embodiment of the present invention.

A graph illustrating an output from a remote-detection system, 10 in accordance with the present invention taken when the system was used to illuminate and observe the reflections from a human subject's chest is illustrated in FIG. 3B. The graph 100 contains a series of large features 102 that are spaced approximately 6 seconds apart and are indicative of the respiration of the subject. In addition, the graph 100 contains a number of smaller features 104 that are spaced less than two seconds apart and are indicative of the beating of the subject's heart.

Figure 3C:
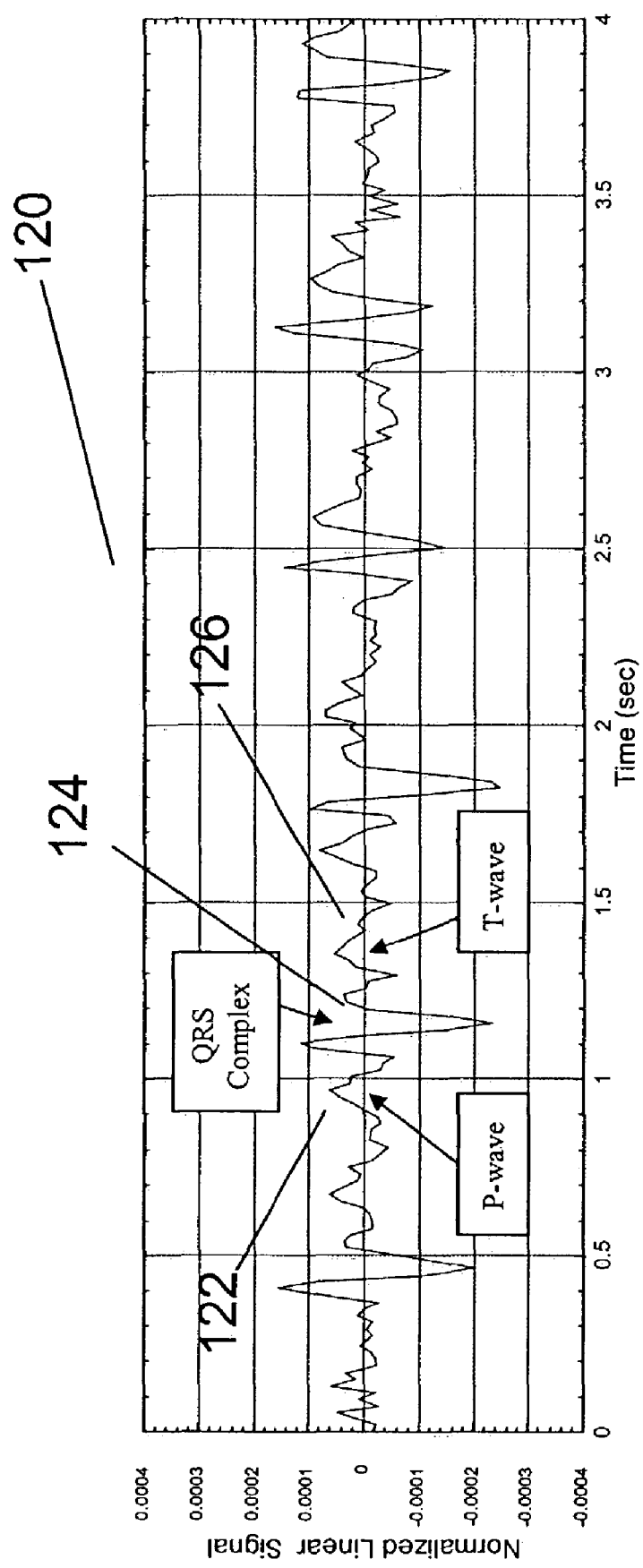
FIG. 3C is a graph showing a signal that results when the signal illustrated in FIG. 3C is low pass filtered and normalized.

A graph of a second output of a remote-detection system, 10 in accordance with the present invention is illustrated in FIG. 3C. The second output has been low-pass filtered to smooth away low frequency signals. An effect of the low-pass filtering is to remove the component 102 of the output illustrated in FIG. 3C that is indicative of the respiration of the subject. The graph 120 shows a series of peaks that correspond to a P-wave 122, a QRS complex 124 and a T-wave 126. The output graphed in FIG. 3C provides information about a portion of the electrophysiology of the heart as it beats. In order to form a complete picture of the heart (i.e. containing at least as much information as a conventional 12-lead electrocardiogram), three orthogonal measurements can be taken using a single or multiple remote-detection systems in accordance with the present invention. Linear algebra can be used to construct the "12-lead" responses from the three orthogonal components measured with the remote-detection system in accordance with the present invention, to build a complete impression of the electrophysiology of the heart as it beats.

As discussed above, a remote-detection system in accordance with the present invention is capable of obtaining a considerable amount of information concerning a subject. The particular information obtained by the remote-detection system is dependant upon the application. In one embodiment, the detector monitors a subject's respiration and pulse rates. In other embodiments, the detector can obtain an electrocardiogram or monitor muscular or neural function. Alternatively, a detector in accordance with the present invention may simply detect the presence of a living creature either as a security device or to assist rescuers in locating trapped or unconscious people.

In many embodiments involving a human subject, the signal generated by the remote-detection system is in a frequency range of 10 GHz to 80 GHz with a beam width of three feet at a distance of 26 feet. Typically, a three foot wide beam is sufficient to localize a single person without interference. In other embodiments, signals in the range of 1 GHz to 100 GHz can be used. Alternatively, embodiments could use signals in the range of 100 MHz to 200 GHz.

The width of the beam required depends on the application. For example, a broad beam could be used where a detector is attempting to detect the presence of a life form in a collapsed building. A narrow beam could then be used to determine the specific location of the detected life form. In medical diagnostic applications, an appropriate beam would have sufficient width to obtain reflections from the required portions of the subject's body and be sufficiently narrow to avoid unwanted reflections. Where Microwave Monolithic Integrated Circuit ("MMIC") technology is used to construct remote-detection systems in accordance with the present invention, two patch antennas separated by four inches could produce the three foot wide beam described above. The effective range of the system would effectively scale with antenna size and transmitted power. Where antenna size is an issue, increasing the frequency of the electromagnetic radiation would enable the construction of smaller antennas. However, the amplitude of the reflected signals will typically decrease as the frequency of the signal increases.

The ability of a remote-detection system in accordance with the present invention to operate through structures or debris is dependent upon the materials composing the structures or debris. Many materials such as bricks, wood or cinderblocks are transparent to electromagnetic signals of frequencies in the ranges described above. However, water in concrete and the presence of metal can interfere with the signals received by the remote-detection system.

In other embodiments, remote-detection systems in accordance with the present invention can be used to monitor neural or muscular function. In addition, a remote-detection system could also be used as a monitor for sudden infant death syndrome or for sleep apnea. The applications of the remote-detection system also include exercise equipment, where the remote-detection system can be used to monitor pulse and/or respiration during an aerobic workout. In all instances the remote-detection system is placed a distance from the subject and measurements are made without the need for contact between the system and the subject. The applications of the remote-detection system are not limited to human subjects or human tissue. The devices and principles described above can be equally applied to detection and monitoring of other life forms.

As discussed above, remote-detection systems in accordance with the present invention can work effectively at considerable distances from the subject. A graph illustrating an output from a remote-detection system in accordance with the present invention that was used to monitor the heart rate of a subject located approximately 2 feet from the system is illustrated in FIG. 4A. The graph 160 contains periodic peaks 162 that are spaced less than 1 second apart. These features are indicative of the subject's heart beating.

Figure 4B:
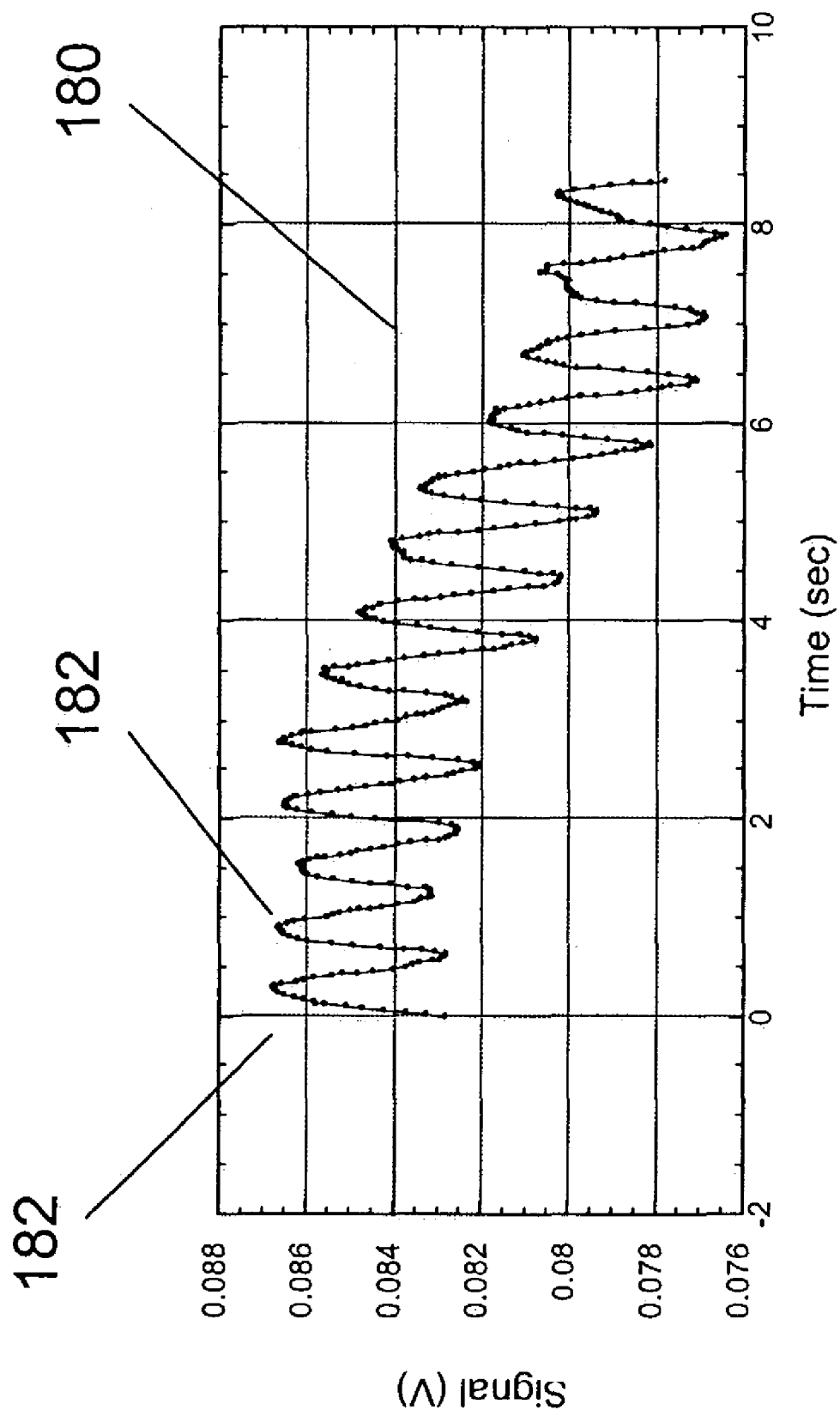
FIG. 4B is a graph illustrating the amplitude of the reflected electromagnetic signal measured in accordance with an embodiment of the present invention from a distance of eight feet.

A graph illustrating an output from a remote-detection system in accordance with the present invention that was used to monitor the heart rate of a human subject located approximately 8 feet from the remote-detection system is illustrated in FIG. 4B. Again, the graph 180 includes a series of periodic peaks 182 spaced less than a second apart. The graph trends downward over a period of eight seconds due to a drift in the DC level of the measurement.

Figure 5:
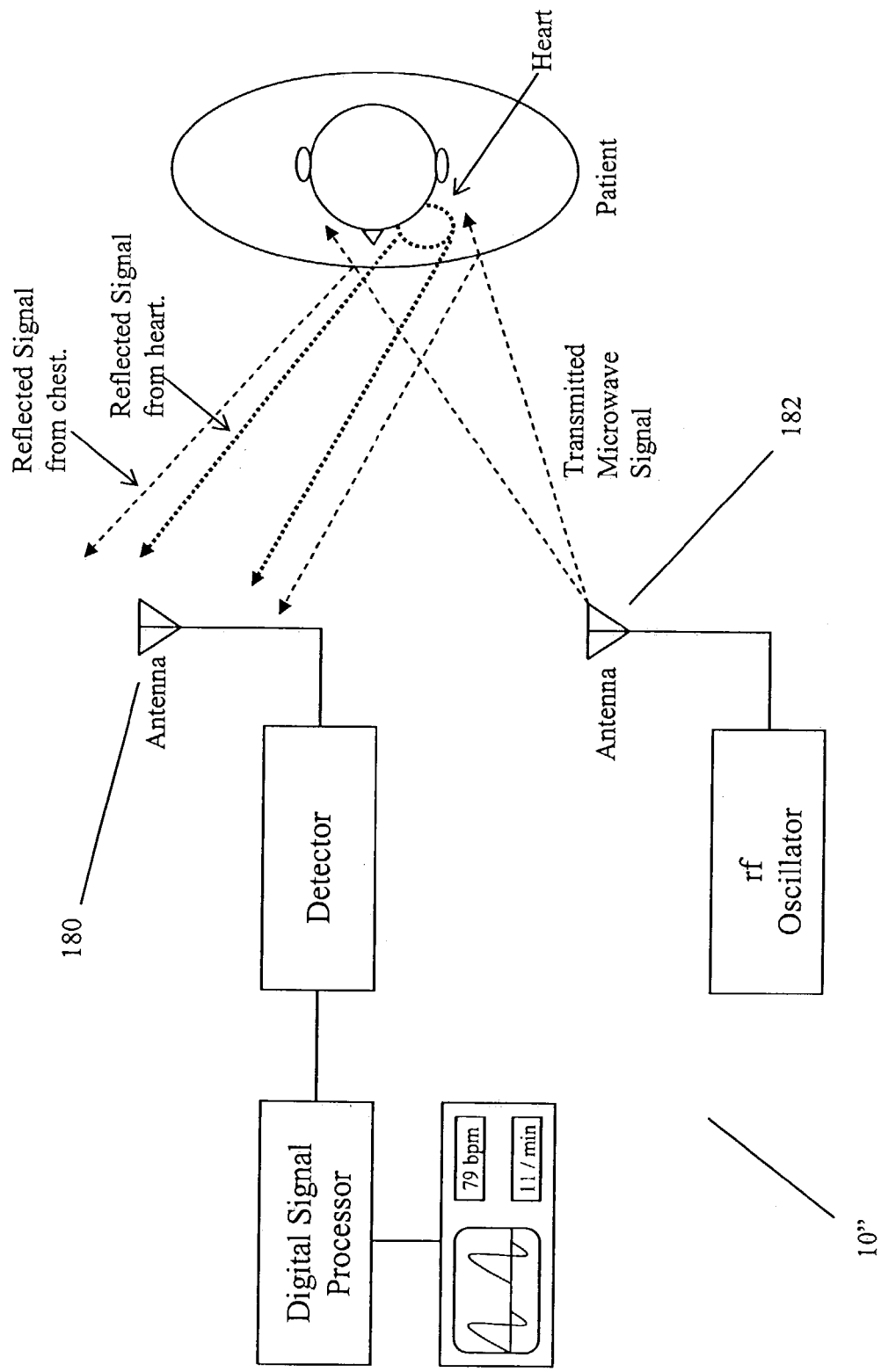
FIG. 5 is a schematic diagram illustrating an embodiment of a detector in accordance with the present invention including separate antennas for generating and detecting an electromagnetic signal.

An embodiment of a remote-detection system in accordance with the present invention that includes separate antennas for illuminating a subject and for receiving reflections is illustrated in FIG. 5. The remote-detection system 10" is similar to the embodiment illustrated in FIG. 1, except that a first antenna 180 is used to generate an electromagnetic signal beam and a second antenna 182 is used to detect the reflected electromagnetic signal beam.

Figure 6:
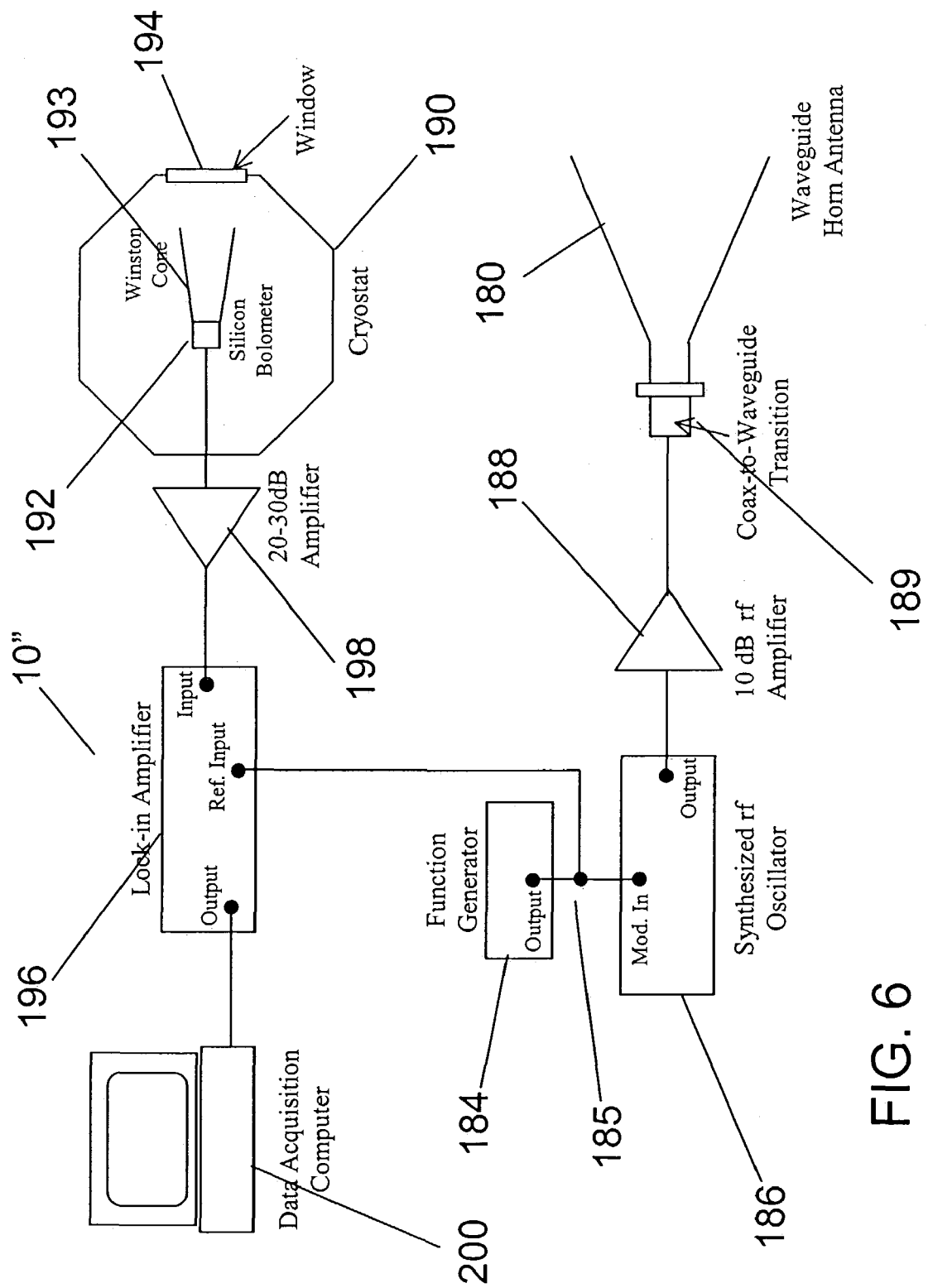
FIG. 6 is a block diagram showing an embodiment of a remote-detection system in accordance with the present invention that includes separate antennas for generating and detecting an electromagnetic signal.

A block diagram of a remote-detection system 10" including two antennas is shown in FIG. 6. The remote-detection system 10" includes a function generator 184 that is connected to a common node 185. A synthesized RF oscillator 186 is also connected to the common node 185 and to a first amplifier 188. The output of the first amplifier is provided to a waveguide horn antenna 180 via a coax-to waveguide transition 189. A second antenna 182 is contained in a cryostat 190 and includes a silicon bolometer 192 and a Winston cone 193. The electromagnetic signal is admitted through a window 194 in the cryostat and outputs from the silicon bolometer are provided to a lock-in amplifier 196 via a second amplifier 198. The lock-in amplifier is connected to the function generator 184 via the common node 185 and to a data acquisition computer 200.

The function generator 184 produces a kilohertz range modulation signal and can be implemented using a Model 33120A manufactured by the Hewlett-Packard Company. The synthesized RF oscillator 186 produces an electromagnetic signal in the range of 20 GHz and can be implemented using a Model 83723B manufactured by the Hewlett-Packard Company. The first amplifier 188 can be implemented using a 10 dB RF amplifier such as a Model 8349B manufactured by the Hewlett-Packard Company. The waveguide horn antenna 180 produces the radiated signal beam and can be implemented using a Model 33120A manufactured by Microlab/FXR of Livingston, N.J. The cryostat with silicon bolometer 182 detects the amplitude of the reflected electromagnetic signal and can be implemented using a Model HDL-5 manufactured by Infrared Laboratories, Inc. of Tucson, Ariz. The lock-in amplifier 196 synchronously detects the kilohertz amplitude-modulated output from the silicon bolometer 192 and can be implemented using a Model SR830 manufactured by Stanford Research Systems. The second amplifier 198 boosts the output of the silicon bolometer 192 and can be implemented using a 20-30 dB amplifier such as a Model LN-6C manufactured by Infrared Laboratories, Inc. The data acquisition computer 200 is implemented using a Macintosh 8600/300, manufactured by Apple Computer, Inc.

While the above description contains many specific embodiments of the invention, these should not be construed as limitations on the scope of the invention, but rather as an example of one embodiment thereof. Many other variations are possible, including implementing remote-detection systems in accordance with the present invention using planar antennas and MMIC manufacturing techniques. In addition, any process, physiological or otherwise, can be monitored that involves variations in patterns and/or intensity of reflected electromagnetic radiation using remote-detection systems in accordance with the present invention. Accordingly, the scope of the invention should be determined not by the embodiments illustrated, but by the appended claims and their equivalents.

What is claimed is:

1. A remote-detection system for monitoring changes in complex impedance associated with physiological activity of a subject that is free to move, comprising:
   a source containing an oscillator configured to illuminate tissue of the subject with an electromagnetic signal beam;
   a receiver configured to receive reflections of the electromagnetic signal beam from the subject, where the reflections include amplitude variations indicative of motion of the subject and amplitude variations indicative of time dependent variations in the complex impedance of the illuminated tissue associated with electrical activity of the subject's heart; and
   a detector connected to the receiver and configured to extract from the reflected signal beam the variations in amplitude indicative of time dependent variations in the complex impedance of the illuminated tissue associated with the electrical activity of the subject's heart.

2. The remote-detection system of claim 1, wherein:
   the source also includes a first antenna portion; and
   the receiver includes a second antenna portion connected to the detector.

3. The remote-detection system in claim 2, wherein the source and the receiver are directionally coupled to a single antenna that acts as the first and second antenna portions.

4. The remote-detection system of claim 1, wherein:
   the subject has a beating heart;
   the complex impedance of the illuminated tissue of the subject changes as the heart beats;
   the amplitude of the reflected electromagnetic signal beam changes as the complex impedance of the illuminated the tissue changes; and
   the detector is configured to extract from the reflected electromagnetic signal beam variations in amplitude associated with the changes in the complex impedance of the illuminated tissue.

5. The remote-detection system of claim 4, further comprises signal processing circuitry connected to the filter and configured to extract an electrocardiographic waveform from the reflected electromagnetic signal beam.

6. The remote-detection system of claim 5, wherein the signal processing circuitry comprises an analog to digital converter and a microprocessor.

7. The remote-detection system of claim 1, wherein:
   the source is configured to generate an electromagnetic signal beam at a predetermined frequency;
   the receiver is configured to amplify the predetermined frequency of the received reflections; and
   the receiver is configured to filter the amplified signal to remove noise.

8. A remote-detection system for monitoring the physiological activity of a subject, comprising:
   means for illuminating at tissue of the subject with an electromagnetic signal;
   means for detecting reflections of the electromagnetic signal, where the reflections include amplitude variations indicative of motion of the subject and amplitude variations indicative of time dependent variations in the complex impedance of the illuminated tissue with respect to the electrical activity of the subject's heart; and
   means for extracting a signal indicative of the changes in the amplitude of the electromagnetic signal reflected by the subject that are associated with time dependent changes in the complex impedance of the illuminated tissue with respect to the electrical activity of the subject's heart.

9. A method of observing changes in the complex impedance of a subject associated with physiological activity, comprising:
   illuminating tissue of the subject with an electromagnetic signal beam;
   receiving reflections of the electromagnetic signal beam that include amplitude variations indicative of motion of the subject and amplitude variations indicative of time dependent variations in the complex impedance of the illuminated tissue associated with electrical activity of the subject's heart; and extracting from the reflected signal a signal indicative of the changes in the amplitude of the electromagnetic signal associated with time dependent changes in the complex impedance of the illuminated tissue associated with the electrical activity of the subject's heart.

10. The method of claim 9, further comprising observing the electromagnetic signal reflected by changes in the complex impedance of the illuminated tissue of the subject.

11. The method of claim 10, further comprising filtering the observed electromagnetic signal to remove components of the reflected signal associated with movement of the subject.

12. The method of claim 9, further comprising producing an electrocardiographic waveform from the extracted signal.

* * * * *